US006398870B1

(12) United States Patent
Kaya et al.

(10) Patent No.: US 6,398,870 B1
(45) Date of Patent: Jun. 4, 2002

(54) COATING DEFECT DETECTING AND MARKING SYSTEM

(75) Inventors: Toshiyuki Kaya; Motoaki Fuchiwaki, both of Hiroshima-ken (JP)

(73) Assignee: Chuo Electronic Measurement Co., Ltd., Hiroshima-ken (JP)

( * ) Notice: Subject to any disclaimer, the term of this patent is extended or adjusted under 35 U.S.C. 154(b) by 0 days.

(21) Appl. No.: 09/425,752

(22) Filed: Oct. 22, 1999

(30) Foreign Application Priority Data

May 25, 1999 (JP) .......................................... 11-145230

(51) Int. Cl.⁷ .............................. B05B 3/00; B05B 9/06
(52) U.S. Cl. ...................... 118/323; 118/670; 118/712; 118/713
(58) Field of Search .................................. 118/712, 713, 118/670, 668, 323, 326

(56) References Cited

U.S. PATENT DOCUMENTS 3,673,493 A * 6/1972 Hoffman et al. ............... 324/37
3,753,085 A * 8/1973 Morton et al. ................. 324/37
5,645,895 A * 7/1997 Murayama et al. .......... 427/424
5,726,705 A * 3/1998 Imanishi et al. ............... 348/92
5,733,374 A * 3/1998 Ekenberb ..................... 118/323
5,734,742 A   3/1998 Asaeda et al.
6,013,308 A * 1/2000 Saito ........................... 118/670

* cited by examiner

Primary Examiner—Richard Crispino
Assistant Examiner—Yewebdar T Tadesse
(74) Attorney, Agent, or Firm—Jordan and Hamburg LLP

(57) ABSTRACT

A coating defect detecting and marking system is provided for automatic detection and marking of a coating defect on the body surface of a car. The system detects a spot to mend such as a flaw or coating defect on the outer surface of a coated car body and marks the position of the spot to mend. There are provided along a production line along which the car body is conveyed an imaging block to detect a spot to mend such as a flaw or coating defect on the outer surface of the coated car body, and a piezo pump to provide a jet of marking solution to a corresponding position on the car body surface to the spot to mend detected by the imaging block.

24 Claims, 2 Drawing Sheets

COATING DEFECT DETECTING AND MARKING SYSTEM

BACKGROUND OF THE INVENTION

1. Field of the Invention

The present invention relates to a coating defect detecting and marking system for detecting a flaw, coating defect or the like on the outer surface of a coated vehicle or car, for example, and marking the actual position of such a defect on the car body surface for the convenience of subsequent mending or retouching.

2. Description of Related Art

Conventionally, to mend or retouch a flaw or a coating defect caused by mixing of dust, dirt or bubble in the coating film on a coated car body surface, the car body surface is checked using a car body appearance tester, for example, and test results thus obtained, for example, information on the position and size of such a flaw or coating defect on the car body surface is displayed on a CRT screen or recorded by printing in a car body development. Based on the test data thus displayed or recorded, the worker in charge of the mending or retouching locates the flaw or defect on the car body surface and manually marks the actual position thereof on the car body surface.

That is, the position and size of a flaw or coating defect on the car body surface can be detected and acquired by the car body appearance tester, but they have to be marked by hand on the actual car body surface after all for mending or retouching the flaw or defect. Such marking work is troublesome and further there may possibly be an error between the detected position included in the test data and the actual position of the flaw or defect on the car body surface.

OBJECT AND SUMMARY OF THE PRESENT INVENTION

Accordingly, the present invention has an object to overcome the above-mentioned drawbacks of the prior art by providing a coating defect detecting and marking system adapted to detect a coating defect on a coated car body and mark its actual position on the car body surface automatically and accurately.

The above object can be attained by providing a coating defect detecting and marking system for detecting on the outer surface of a coated car body a flaw or coating defect to mend or retouch and marking it on the car body surface, the system comprising, according to the present invention:

an image pickup means provided along a production line along which the coated car body is conveyed to detect a defective spot to mend or retouch such as a flaw or coating defect on the car body surface; and a marking means also provided along the production line to provide a jet of a marking solution for marking the detected defective spot in its actual position and/or size on the car body surface.

According to the present invention, the marking of a coating defect on the car body surface can be done automatically with a high accuracy and reliability.

These objects and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Figure 1:
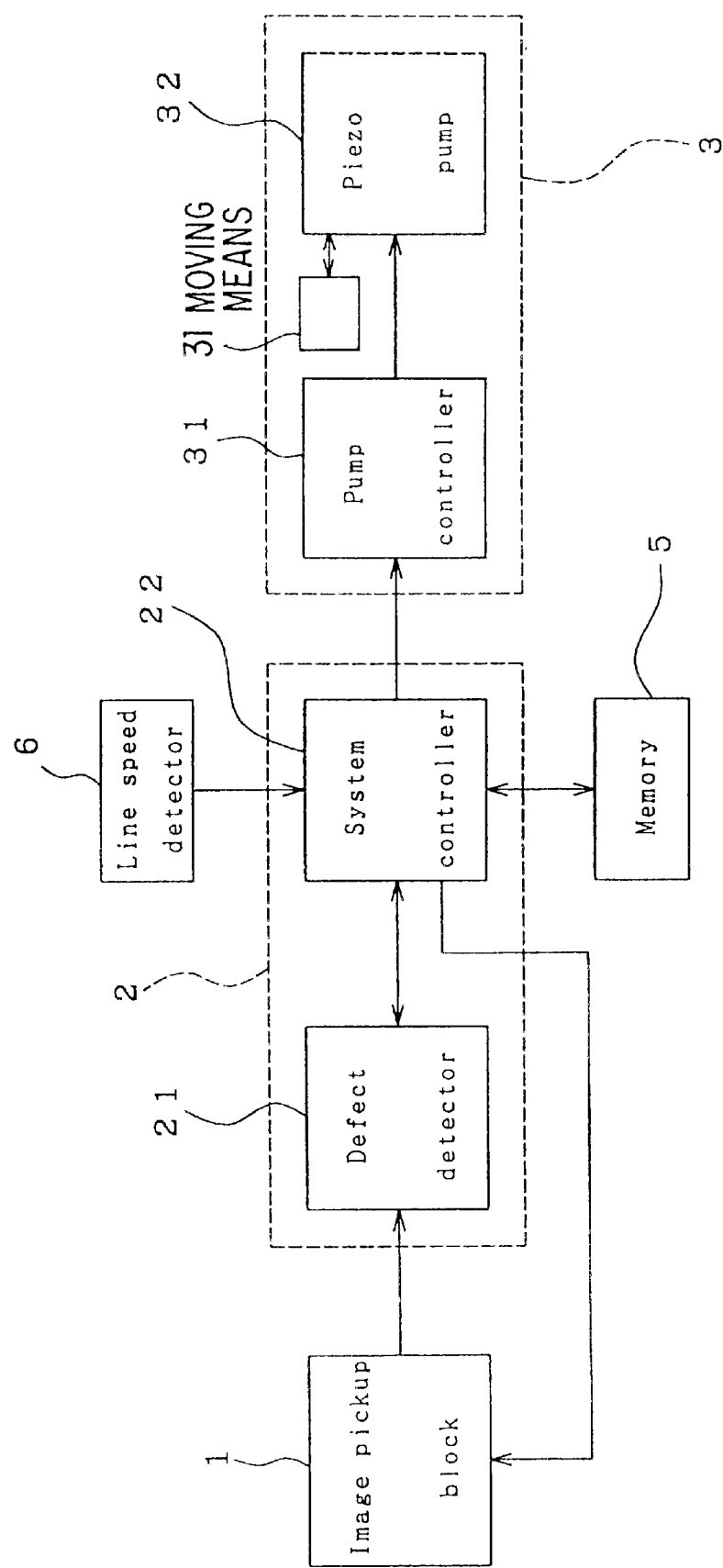
FIG. 1 is a schematic block diagram of the coating defect detecting and marking system according to the present invention.

Referring now to FIG. 1, there is schematically illustrated in the form of a block diagram the coating defect detecting and marking system according to the present invention. As shown, the system comprises mainly an image pickup block 1, control block 2, and a marking block 3.

Figure 2:
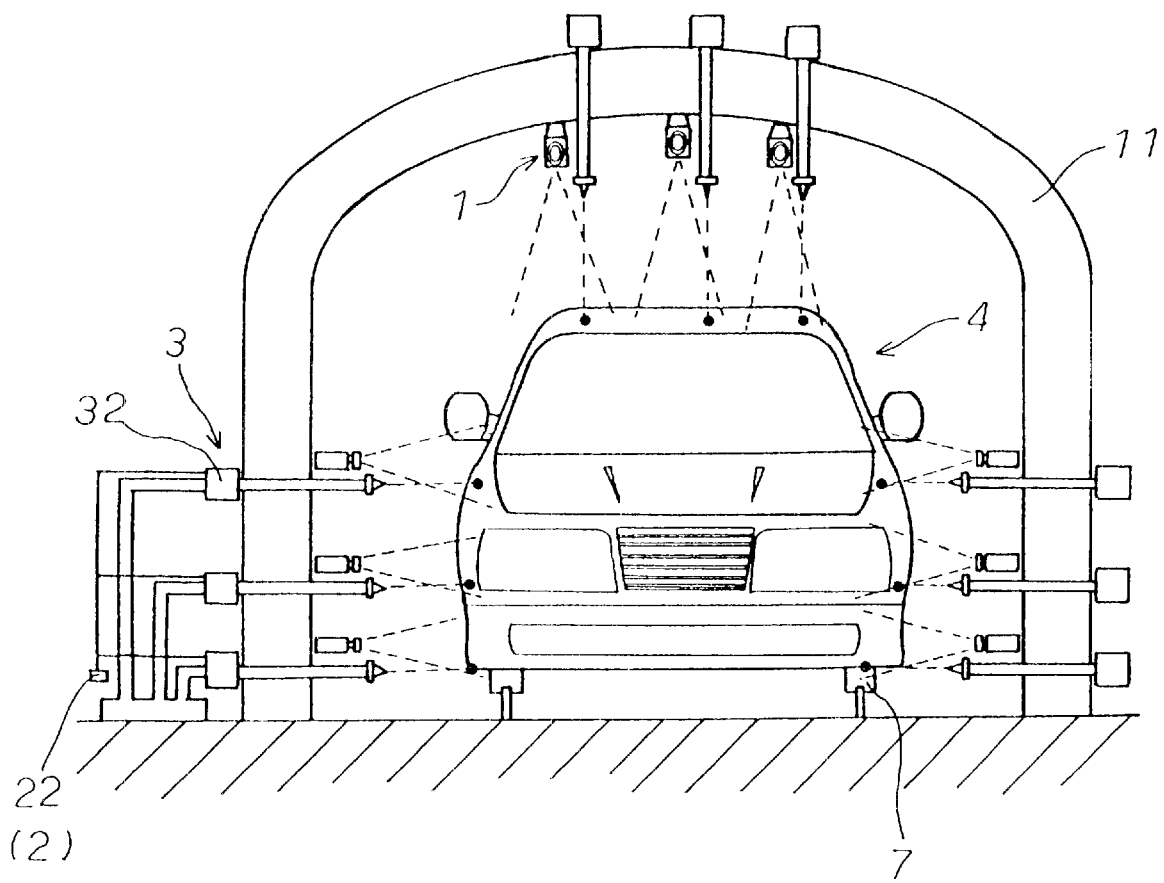
FIG. 2 is a front view of the system according to the present invention.

As shown in FIG. 2, the image pickup block 1 is provided for picking up an image of each of front, side, top and rear surfaces of a car body 4 arriving from a coating post to identify the general shape of the car body 4 and detect any flaw arisen before coating or any coating defect such as dirt, dust or bubble mixed in the coating film during coating (will collectively be referred to as "spot to mend" hereinafter).

In this embodiment, the image pickup block 1 uses CCD cameras. As seen from FIG. 2, twenty to forty CCD cameras are disposed equidistantly from each other on the upper and lateral portions of an arched support 11 fixed on the floor, for example. Note that the support 11 used in this embodiment is formed to have a sufficient size to accommodate all car bodies to be subjected to this checking for spots to mend. The reference 7 in FIG. 2 indicates a production line (belt conveyor) along which the car bodies are conveyed.

The control block 2 comprises a defect detector 21 and system controller 22. The image pickup block 1 is operated under the control of the system controller 22, and an image data acquired by the image pickup block 1 is appropriately processed by the defect detector 21 for finding a spot to mend in the image. Simultaneously with the detection of a spot to mend, the defect detector 21 sets an area corresponding to the general shape of the car body 4 imaged by the image pickup block 1 and detects a spot to mend within the area corresponding to the general shape of the car body 4.

The data of the spot to mend detected by the defect detector 21 is supplied to the system controller 22 which will control the marking block 3 based on the received data from the defect detector 21 and temporarily store all the supplied spots to mend together into a memory 5.

The marking block 3 provides a jet of marking solution for marking the actual position and/or size on the car body surface correspondingly to the detected defective spot to mend. In this embodiment, the marking block 3 comprises a pump controller 31 and piezo pumps 32 which are operated under the control of the pump controller 31. Note that the present invention is not limited to the piezo pump 32 but may use any other means or applicator, such as a solenoid valve, piezo pump and nozzle, or the like.

In this embodiment, each of the piezo pumps 32 of the marking block 3 is disposed in the proximity of each CCD camera of the imaging block 1, for example, disposed a predetermined distance (D) downstream of the imaging block 1 along the production line 7 as shown in FIG. 2. The piezo pumps 32 provide a jet of the marking solution, and the jet position of the piezo pumps 32 is movable in accordance with the width of the car body which is to be inspected. Also, each of the piezo pumps 32 has a nozzle extending perpendicularly to the car body surface as shown, and nozzle end is movable to keep distance of always about 20 cm between the nozzle end and car body surface. An air cylinder controlled by the pump controller 31 may be provided to move towards and away from the car body each of those of the nozzles which are laid extending horizontally in relation to the lateral sides of the car body. This is intended to accommodate the difference in body width from one to another type of car under this inspection. Namely, this arrangement keeps the distance between the nozzle end and car body lateral side constant. The marking block 3 may additionally comprise a relocating mechanism or inching mechanism 33 for each piezo pump 32. The mechanism 33 can be appropriately activated to move the piezo pump 32 from its home position to a spot to mend (namely, a flaw or defect) or pivot the piezo pump 32 towards the spot.

Since some of the coatings on the car body surfaces are very susceptible to flaw and the marking solution should be easily removable by wiping even after it is dried, the present invention uses a marking solution which is an ultra-fine grain compound solution having a color pigment such as a paint mixed therein.

Further, the coating defect detecting and marking system according to the present invention comprises a line speed detector 6 annexed to the control block 2. The line speed detector 6 is an encoder, for example. It is provided to detect a speed of the car body 4 being conveyed along the production line 7 (belt conveyor) after subjected to coating, namely, a line speed (V), and pre-calculate a time from detection of a spot to mend by the imaging block 1 until the spot to mend arrives at a region where it is aligned with the piezo pump 32, that is, a time ($t_0$) at which the piezo pump 32 is put into operation. According to this embodiment, since the piezo pump 32 is located a predetermined distance (D) downstream of the imaging block 1 along the production line 7, the time to at which the piezo pump 32 is activated after the spot to mend is detected by the imaging block 1 is calculated to be $t_0 = D/V$. The activation time ($t_0$) calculated by the line speed detector 6 and the data of the spot to mend detected by the defect detector 21 are supplied to the system controller 22 which in turn will control the marking block 3 based on the supplied activation time and spot data.

More particularly, the image data acquired by the imaging block 1 is processed immediately by the defect detector 21, then used to locate the spot to mend on the car body surface, and supplied to the system controller 22. The activation time ($t_0$) set by the line speed detector 6 is supplied to the system controller 22 in advance, and in the predetermined time ($t_0$) from the detection of the spot to mend, the piezo pump 32 is activated to provide a jet of the marking solution towards the car body surface. Namely, when the spot to mend detected by the imaging block 1 passes by the region where it is just aligned with the piezo pump 32, the piezo pump 32 provides the jet of marking solution.

In this embodiment, the marking solution will be applied in the form of a circle of about 5 mm in diameter precisely onto the detected spot to mend in the image data acquired by the imaging block 1 or to the vicinity of the spot. Thus the spot to mend such as a flaw or coating defect can easily be found on the car body surface.

The embodiment of the present invention uses a marking solution easily removable by wiping. After the spot to mend such as flaw or coating defect is mended, the marking solution can be removed by wiping without any damage to the car body surface. The color pigment contained in the marking solution permits easy location of the spot to mend with also no risk of oversight. That is, the marking solution used with the defect detecting and marking system according to the present invention is highly reliable.

In the forgoing, the embodiment is adapted to provide a jet of the marking solution onto the spot to mend on the car body surface or to the vicinity of the spot. However, the present invention may be adapted such that the marking solution is applied to cover an entire spot to mend on the car body surface. The aforementioned embodiment is adapted to detect and mark a defect on the car body surface after being coated with a paint. However, the present invention is applicable to a surface checking of a car body before being coated with a paint.

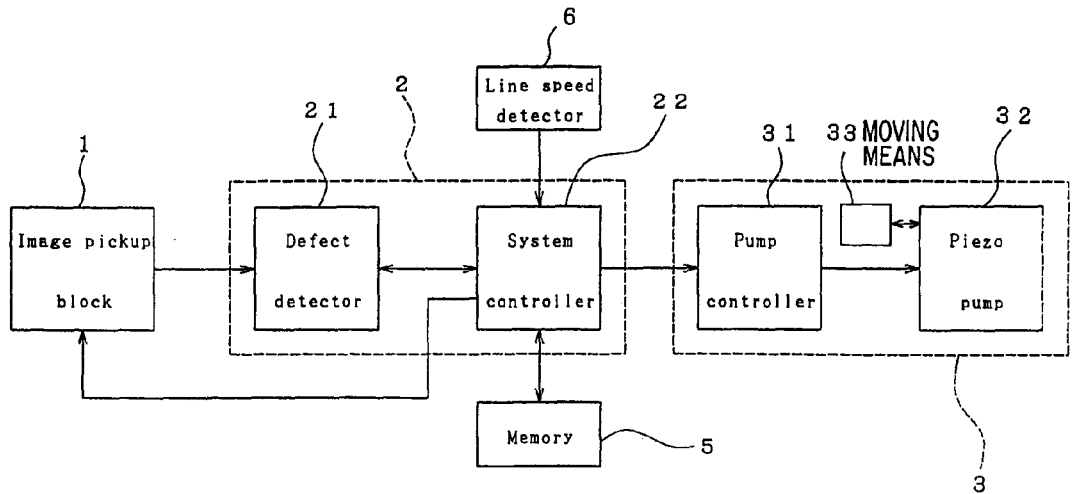

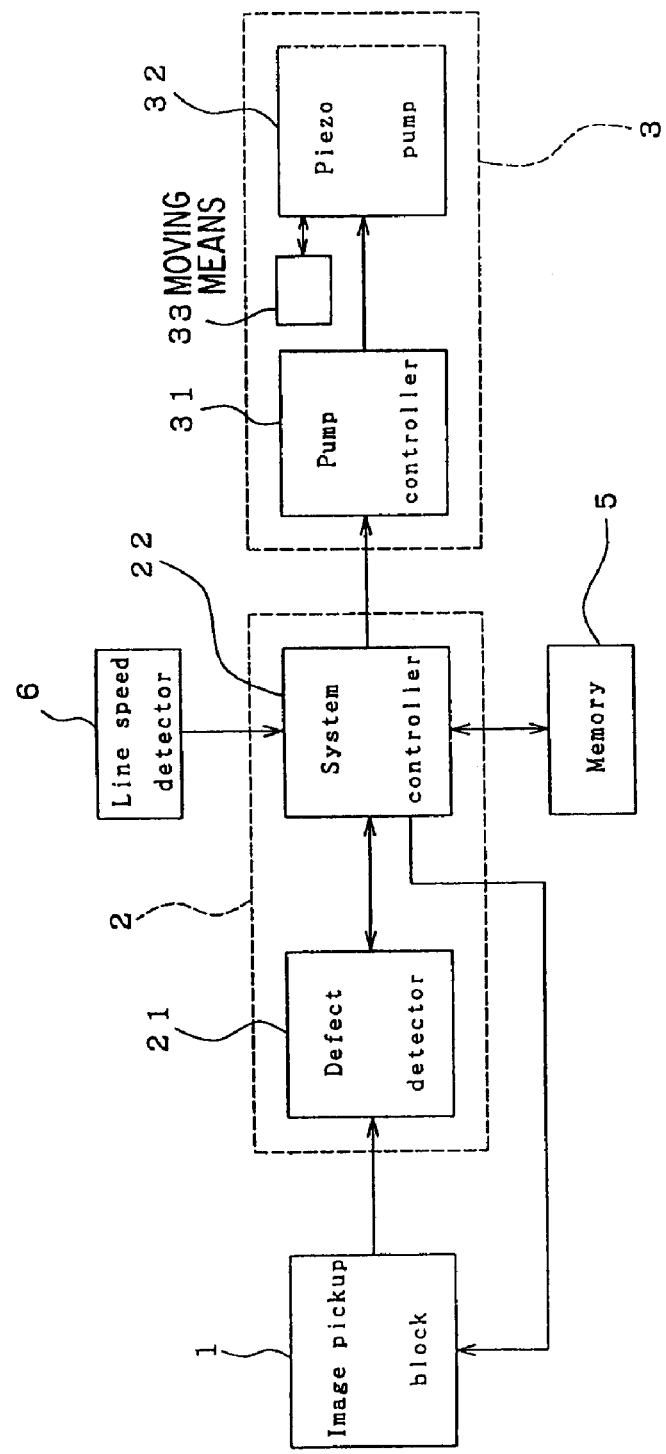

What is claimed is:

1. A coating defect detecting and marking system for detecting on the outer surface of a coated car body a flaw or coating defect to mend and marking it on the car body surface, the system comprising:
    an image pickup means provided along a production line along which the coated car body is conveyed to detect a defective spot to mend such as a flaw or coating defect on the car body surface;
    a marking mews also provided along the production line including a nozzle to provide a jet of a marking solution for marking the detected defective spot in its actual position and/or size on the car body surface; and
    the marking means including a moving means for moving the nozzle, based on imaged data, to direct the jet of the marking solution at the detected defective spot.

2. The coating defect detecting and marking system according to claim 1, wherein the moving means includes a transport device to move the nozzle toward the detective spot for marking.

3. The coating defect detecting and marking system according to claim 2, wherein the marking solution is removable by wiping after drying.

4. The coating defect detecting and marking system according to claim 3, wherein the marking solution has a grain compound having a pigment.

5. The coating defect detecting and marking system according to claim 1, wherein the moving means includes a pivoting device to pivot the jet produced by the marking means toward the defective spot for marking.

6. The coating defect detecting and marking system according to claim 5, wherein the marking solution is removable by wiping after drying.

7. The coating defect detecting and marking system according to claim 6, wherein the marking solution has a grain compound having a pigment.

8. The coating defect detecting and marking system according to claim 1, wherein the marking solution is removable by wiping after drying.

9. The coating defect detecting and marking system according to claim 8, wherein the marking solution has a grain compound having a pigment.

10. A defect detecting and marking system for detecting a spot to mend on an outer surface of a coated body and marking the spot to mend, the system comprising:
    an image pickup device moved relative the coated body for detecting a spot to mend on the coated body;
    a marking unit moved relative the coated body having a marking solution applicator for making the spot to mend using a marking solution;
    a relocating mechanism for moving the marking solution applicator to apply the marking solution at the spot to mend; and
    a controller for controlling the marking unit and the relocating mechanism to apply the marking solution at the spot to mend based on output from the image pickup device.

11. The coating defect detecting and marking system according to claim 10, wherein the relocating mechanism moves the marking solution applicator to the spot to mend.

12. The coating defeat detecting and marking system according to claim 11, wherein the marking solution is removable by wiping after drying.

13. The coating defect detecting and marking system according to claim 12, wherein the marking solution has a grain compound having a pigment.

14. The coating defect detecting and marking system according to claim 10, wherein the relocating mechanism pivots the marking solution applicator to apply the marking solution at the spot to mend.

15. The coating defect detecting and marking system according to claim 14, wherein the marking solution is removable by wiping after drying.

16. The coating defect detecting and marking system according to claim 15, wherein the marking solution has a grain compound having a pigment.

17. The coating defect detecting and marking system according to claim 10, wherein the marking solution is removable by wiping after drying.

18. The coating defect detecting and marking system according to claim 17, wherein the marking solution has a grain compound having a pigment.

19. The coating defect detecting and marking system according to claim 1, wherein the image pickup means is proximate the markings.

20. The coating defect detecting and marking system according to claim 1, wherein the image pickup means is a CCD camera.

21. The coating defect detecting and marking system according to claim 1, wherein the marking means includes an air cylinder for maintaining a predetermined distance between the marking means and the car.

22. The coating defect detecting and marking system according to claim 10, wherein the image pickup device is proximate the marking unit.

23. The coating defect detecting and marking system according to claim 10, wherein the image pickup device is a CCD camera.

24. The coating defect detecting and marking system according to claim 10, wherein the marking unit includes a movable nozzle and an air cylinder for maintaining a predetermined distance between the marking unit and the body.

* * * * *

UNITED STATES PATENT AND TRADEMARK OFFICE
CERTIFICATE OF CORRECTION

PATENT NO.   : 6,398,870 B1
DATED        : June 4, 2002
INVENTOR(S)  : Kaya et al.

It is certified that error appears in the above-identified patent and that said Letters Patent is hereby corrected as shown below:

Title page,
The title page, showing an illustrative figure, should be deleted and substitute therefor the attached title page.

Drawings,
Delete Figure 1, and substitute therefor the Figure, consisting of Figure 1, as shown on the attached pages.

Signed and Sealed this

Twelfth Day of November, 2002

Attest:

Attesting Officer

JAMES E. ROGAN
Director of the United States Patent and Trademark Office

(12) United States Patent
Kaya et al.

(10) Patent No.: US 6,398,870 B1
(45) Date of Patent: Jun. 4, 2002

(54) COATING DEFECT DETECTING AND MARKING SYSTEM

(75) Inventors: Toshiyuki Kaya; Motoaki Fuchiwaki, both of Hiroshima-ken (JP)

(73) Assignee: Chuo Electronic Measurement Co., Ltd., Hiroshima-ken (JP)

( * ) Notice: Subject to any disclaimer, the term of this patent is extended or adjusted under 35 U.S.C. 154(b) by 0 days.

(21) Appl. No.: 09/425,752

(22) Filed: Oct. 22, 1999

(30) Foreign Application Priority Data

May 25, 1999 (JP) .............................. 11-145230

(51) Int. Cl.⁷ .............................. B05B 3/00; B05B 9/06
(52) U.S. Cl. .................. 118/323; 118/670; 118/712; 118/713
(58) Field of Search .................. 118/712, 713, 118/670, 668, 323, 326

(56) References Cited

U.S. PATENT DOCUMENTS 3,673,493 A * 6/1972 Hoffman et al. .............. 324/37
3,753,085 A * 8/1973 Morton et al. ................ 324/37
5,645,895 A * 7/1997 Murayama et al. .......... 427/424
5,726,705 A * 3/1998 Imanishi et al. ............... 348/92
5,733,374 A * 3/1998 Ekenberb ..................... 118/323
5,734,742 A   3/1998 Asaeda et al.
6,013,308 A * 1/2000 Saito ........................... 118/670

* cited by examiner

*Primary Examiner*—Richard Crispino
*Assistant Examiner*—Yewebdar T Tadesse
(74) *Attorney, Agent, or Firm*—Jordan and Hamburg LLP

(57) ABSTRACT

A coating defect detecting and marking system is provided for automatic detection and marking of a coating defect on the body surface of a car. The system detects a spot to mend such as a flaw or coating defect on the outer surface of a coated car body and marks the position of the spot to mend. There are provided along a production line along which the car body is conveyed an imaging block to detect a spot to mend such as a flaw or coating defect on the outer surface of the coated car body, and a piezo pump to provide a jet of marking solution to a corresponding position on the car body surface to the spot to mend detected by the imaging block.

24 Claims, 2 Drawing Sheets